United States Patent
Lee

(10) Patent No.: US 8,211,673 B2
(45) Date of Patent: Jul. 3, 2012

(54) COMPOSITION AND METHOD FOR SEQUENCING NUCLEIC ACID

(75) Inventor: Linda G. Lee, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 345 days.

(21) Appl. No.: 12/365,140

(22) Filed: Feb. 3, 2009

(65) Prior Publication Data

US 2009/0215062 A1    Aug. 27, 2009

Related U.S. Application Data

(60) Provisional application No. 61/026,085, filed on Feb. 4, 2008.

(51) Int. Cl.
*C12P 19/34* (2006.01)
*C12Q 1/68* (2006.01)

(52) U.S. Cl. .................................. 435/91.1; 435/6.1

(58) Field of Classification Search .................. None
See application file for complete search history.

(56) References Cited

U.S. PATENT DOCUMENTS

| | | | |
|---|---|---|---|
| 5,741,676 | A | 4/1998 | Fuller |
| 5,756,285 | A | 5/1998 | Fuller |
| 5,849,487 | A | 12/1998 | Hase et al. |
| 6,379,940 | B2 | 4/2002 | Moffett et al. |
| 6,387,634 | B2 | 5/2002 | Moffett et al. |

FOREIGN PATENT DOCUMENTS

| | | |
|---|---|---|
| WO | WO-99/34014 | 7/1999 |
| WO | WO-9934014 | 7/1999 |
| WO | WO-2006/073892 | 7/2006 |
| WO | WO-2009/100080 | 8/2009 |

OTHER PUBLICATIONS

Dean, F. B. "Rapid amplification of plasmid and phage DNA using Phi 29 DNA polymerase and multiply-primed rolling circle amplification", *Genome research* Jun. 2001, pp. 1095-1099.
Kim, "One-Step enzymatic purification of PCR products for direct sequencing", *Current protocols in human genetics*, Aug. 2001.
PCT Application No. PCT/US2009/032989, International Search Report, mailed Jun. 22, 2009.
PCT Application No. PCT/US09/032989, International Preliminary Report on Patentability, dated Aug. 19, 2010.

*Primary Examiner* — Christopher M Babic

(57) ABSTRACT

A composition for sequencing DNA is provided and comprises a nuclease and a nuclease-resistant sequencing primer. A method of preparing DNA for sequencing and a method of sequencing DNA are also provided. The method of sequencing DNA can comprise contacting amplification reaction products with the composition under conditions in which excess amplification primer is degraded by the nuclease and the nuclease-resistant sequencing primer is essentially non-degraded.

26 Claims, 12 Drawing Sheets

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial
<220> FEATURE:
<223> OTHER INFORMATION: Synthetic

<400> SEQUENCE: 1
tgtaaaacga cggccagt                                                       18

<210> SEQ ID NO 2
<211> LENGTH: 18
<212> TYPE: DNA
<213> ORGANISM: Artificial
<220> FEATURE:
<223> OTHER INFORMATION: Synthetic

<400> SEQUENCE: 2
caggaaacag ctatgacc                                                       18

<210> SEQ ID NO 3
<211> LENGTH: 18
<212> TYPE: DNA
<213> ORGANISM: Artificial
<220> FEATURE:
<223> OTHER INFORMATION: Synthetic

<400> SEQUENCE: 3
caggaaacag ctatgacc                                                       18

<210> SEQ ID NO 4
<211> LENGTH: 18
```

```
<212> TYPE: DNA
<213> ORGANISM: Artificial
<220> FEATURE:
<223> OTHER INFORMATION: Synthetic

<400> SEQUENCE: 4
tgtaaaacga cggccagt                                                    18

<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
ggtagtgccc aaacgctca                                                   19

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
gccttatcgc tgggaaatca                                                  20

<210> SEQ ID NO 7
<211> LENGTH: 762
<212> TYPE: DNA
<213> ORGANISM: Artificial
<220> FEATURE:
<223> OTHER INFORMATION: Synthetic

<400> SEQUENCE: 7
cccgtcgcct tatcgctggg aaatcaggta tcgaatcttt tagctcgtac catgtcctga       60
tacagggctt gataatcatt ttctgaatac attttcgcga taccgtccag cgacattctt      120
cctcggtaca taatctcctt tggcgtttcc cgatgtccgt cacgcacatg ggatcccgtg      180
atgacctcat taaaaacacg ctgcaatccc tcctcatctt gcaggcaag tccgattttt       240 tgcgttgatt ttttaatgca gaatatgcag ttaccgagat gttccggtat ttgcaaatcg      300
aatggttgtt gcttccacca tgcgaggata tcttccttct caaagtctga cagttcagca      360
agatatctga ttccaggctt tggctttagc cgcttcggtt catcagctct gatgccaatc      420
cacgtggtgt aattccctcg cccgaaatgg tcatcacagt atttggtgaa gggaacgagt      480
tttaatctgt cagtgcagaa cgcgccgccg acgtatggag tgccatattt ctttaccata      540
tcgataaatg gcttcagaac aggcattcgc gtctgaatat ccttcggttc ccataccgta      600
taaccatttg gctgtccaag ctccgggttg atatcaacct gcaatacggt gagcggtata      660
tcccagaact tcacaacttc cctgacaaac cgatatgtca ttggatgttc acaacctgta      720
tccatgaaaa cgtaattgag cgtttgggca ctaccatgcg at                         762

<210> SEQ ID NO 8
<211> LENGTH: 19
<212> TYPE: DNA
<213> ORGANISM: Artificial
<220> FEATURE:
<223> OTHER INFORMATION: Synthetic

<400> SEQUENCE: 8
ggtagtgccc aaacgctca                                                   19
```

```
<210> SEQ ID NO 9
<211> LENGTH: 38
<212> TYPE: DNA
<213> ORGANISM: Artificial
<220> FEATURE:
<223> OTHER INFORMATION: Synthetic

<400> SEQUENCE: 9
tgtaaaacga cggccagtgg ctcctggcac aaagctgg                            38

<210> SEQ ID NO 10
<211> LENGTH: 41
<212> TYPE: DNA
<213> ORGANISM: Artificial
<220> FEATURE:
<223> OTHER INFORMATION: Synthetic

<400> SEQUENCE: 10
caggaaacag ctatgacctg catctcattc tccaggcttc a                        41

<210> SEQ ID NO 11
<211> LENGTH: 630
<212> TYPE: DNA
<213> ORGANISM: Artificial
<220> FEATURE:
<223> OTHER INFORMATION: Synthetic

<400> SEQUENCE: 11
tgtaaaacga cggccagtgg ctcctggcac aaagctggac agtcgccatg acaagtaagg    60
gcaagtaatc cgcctgccgg aggaagcaaa ggaaatggag ttggggagga gggtgcagag   120
tcaggattct cgccgacctg gtgccgtaga tactaacatt ttggggtgga aaattctgca   180
agccagagct gtgagggcag aattggtgga aatcattttg gaggaatcct gcattgtgtc   240
aaatatgaag ggtggaagga agaaagcttt tgcgtttgct ctcagctgga tcctttcttc   300
tcatcagtta aaatgtcatt ttttaggaag gctttccgta atatcacacc ctaacgtttt   360
ctcccagata cttttatatca caccatctta tttaatctcc ttcacaaccc ttatcactct   420
gataagattt atttgttcat tgctttcagt acatggaaac gtaagcctta tgaggatata   480
gaatttttct actatcttat tcattgttgt attcctgagt gcctatatca gtgctgggta   540
gcaagtaaga gctcgataat aaatatttt tgaatgaggg agacaggtct gaagcctgga   600
gaatgagatg caggtcatag ctgtttcctg                                   630

<210> SEQ ID NO 12
<211> LENGTH: 18
<212> TYPE: DNA
<213> ORGANISM: Artificial
<220> FEATURE:
<223> OTHER INFORMATION: Synthetic

<400> SEQUENCE: 12
tgtaaaacga cggccagt                                                 18
```

COMPOSITION AND METHOD FOR SEQUENCING NUCLEIC ACID

CROSS-REFERENCE TO RELATED APPLICATIONS

This nonprovisional application claims the benefit of U.S. Provisional Application No. 61/026,085, filed Feb. 4, 2008, which is herein incorporated by reference in its entirety.

FIELD

The present teachings pertain to methods of preparing and sequencing DNA. The teachings also relate to a composition for preparing and sequencing DNA.

BACKGROUND

A standard polymerase chain reaction (PCR)/sequencing workflow generally includes three steps requiring reagent addition: an initial PCR step, a cleanup step, and a sequencing step. The PCR step involves amplification of a template polynucleotide using amplification primers and a thermo-stable DNA polymerase enzyme. The cleanup step is commonly done by the addition of exonuclease I and alkaline phosphatase, followed by incubation, and subsequent heat-kill to inactivate the enzymes. A standard PCR/sequencing workflow is illustrated in FIG. 1.

A typical PCR reaction uses an excess of amplification primers, some which remain even upon completion of the reaction. This necessitates removal of the excess primers before proceeding to a sequencing reaction, because the excess amplification primers will interfere with a subsequent sequencing reaction. A PCR reaction furthermore contains an excess of dNTPs that can interfere with a subsequent sequencing reaction. The hydrolytic properties of exonuclease I degrade single-stranded DNA present in the PCR mixture allowing the amplification product (amplicon) to be used more efficiently in subsequent sequencing applications. The enzyme activity of alkaline phosphatase dephosphorylates dNTPs remaining from the PCR reaction. After an appropriate incubation period, the exonuclease I and alkaline phosphatase enzymes are heat inactivated before adding sequencing primer, dNTPs, and ddNTPs-dyes; otherwise the enzymes would degrade these reagents and the sequencing reaction products.

Without adequate exonuclease I and alkaline phosphatase treatment to remove excess PCR amplification primers and dNTPs, aberrant sequence ladders can be generated. For instance, as illustrated in FIG. 1, sequence ladders can be generated from both ends of a DNA sequence, causing overlapping forward and reverse sequence ladders. An excess of dNTPs can produce a weak sequencing signal and/or short sequence reads.

Problems exist in standard PCR/cycle sequencing in that the cleanup step involves an extra reagent addition step in a PCR/cycle sequencing workflow. This extra reagent addition step requires extra labor, increases the chance of introducing errors or cross contamination into the process, and can make automation difficult. A need exists for improved methods of PCR and sequencing.

SUMMARY

According to various embodiments, the present teachings relate to a method of preparing DNA for sequencing, a method of sequencing DNA, and a composition for sequencing DNA. The teachings provide a method of PCR/sequencing (including cycle sequencing) that can be quicker and simpler, and require fewer steps, than traditional methods. The methods of the present teachings utilize a nuclease-resistant sequencing primer in combination with nuclease, which can reduce sequence noise and remove undesired sequence priming. The present teachings further provide a composition for DNA sequencing that can be used with such a method.

According to various embodiments, the present teachings disclose a method of preparing DNA for sequencing. In some embodiments, the DNA preparation method can eliminate at least one reagent addition step used in conventional PCR/cycle sequencing, thereby reducing the number of processing steps.

According to various embodiments, a method of preparing DNA for sequencing is provided that can comprise amplifying DNA under conditions to produce amplification reaction products, the amplification reaction products comprising excess amplification primer, and contacting the amplification reaction products with a reaction mixture comprising a nuclease and a nuclease-resistant sequencing primer, under conditions in which the excess amplification primer is degraded by the nuclease. According to various embodiments, the nuclease-resistant sequencing primer is essentially non-degraded under such conditions. In some embodiments, the excess amplification primer can comprise inter-nucleotide phosphodiester bonds that are susceptible to nuclease cleavage. In some embodiments the nuclease-resistant sequencing primer can comprise at least one inter-nucleotide phosphorothioate bond that is not susceptible to nuclease cleavage.

The present teachings further provide a method of sequencing DNA that can generate clean, clear and accurate sequencing data by a simpler workflow compared to conventional methods, and that requires less time. According to various embodiments, a DNA sequencing method is provided that can comprise adding a sequencing reaction mix directly to a completed PCR amplification reaction, without first performing a separate cleanup step; that is, without first removing excess PCR amplification primers by the addition of a nuclease and completing a nuclease inactivation step, followed by a second addition of sequencing primers and reagents.

According to various embodiments, a method of sequencing DNA is provided that can comprise amplifying DNA in a first reaction mixture comprising nuclease-sensitive amplification primers to form amplified DNA, contacting the first reaction mixture with a second reaction mixture comprising a nuclease and a nuclease-resistant sequencing primer under conditions in which the nuclease-sensitive amplification primers are degraded by the nuclease, inactivating the nuclease, and causing the amplified DNA to serve as template in a sequencing reaction under conditions in which the nuclease-resistant sequencing primer primes the sequencing reaction.

The present teachings further provide a composition for sequencing nucleic acid. According to various embodiments, the composition can comprise a polymerase, a nuclease, a nuclease-resistant sequencing primer, deoxynucleotide triphosphates (dNTPs), and dideoxynucleotide triphosphates (ddNTPs). In various embodiments of the method, the composition can be added in one step directly to a PCR reaction product, without first removing excess PCR amplification primers from the PCR reaction product.

Various patents, patent applications, and other publications are referred to herein, all of which are incorporated herein in their entireties by reference. In addition, the following standard reference works are incorporated herein by reference: Current Protocols in Molecular Biology, John Wiley & Sons, N.Y., edition as of October 2007; Sambrook, Russell, and Sambrook, Molecular Cloning: A Laboratory Manual, 3rd ed., Cold Spring Harbor Laboratory Press, Cold Spring Harbor, 2001. In the event of a conflict between the instant specification and any document incorporated by reference, the specification shall control, it being understood that the determination of whether a conflict or inconsistency exists is within the discretion of the inventors and can be made at any time.

Additional features and advantages of the present teachings will be evident from the description that follows, and in part will be apparent from the description, or can be learned by practice of the present teachings. It is to be understood that both the foregoing summary and the following detailed description are exemplary and explanatory only and are intended to provide further explanation of the present teachings without limiting the present teachings.

DETAILED DESCRIPTION

To facilitate understanding of the present teachings, the following definitions are provided. It is to be understood that, in general, terms not otherwise defined are to be given their ordinary meanings or meanings as generally accepted in the art.

As used herein, the term "PCR/cycle sequencing" refers to a method for determining a nucleotide sequence of DNA by PCR amplifying the DNA, followed by sequencing reactions repeated (or cycled) several times. This cycling is similar to PCR because the sequencing reaction is allowed to proceed at 42° C.-55° C., then stopped at 95° C., and started again at 42° C.-55° C., and uses a thermostable DNA polymerase.

Figure 1:
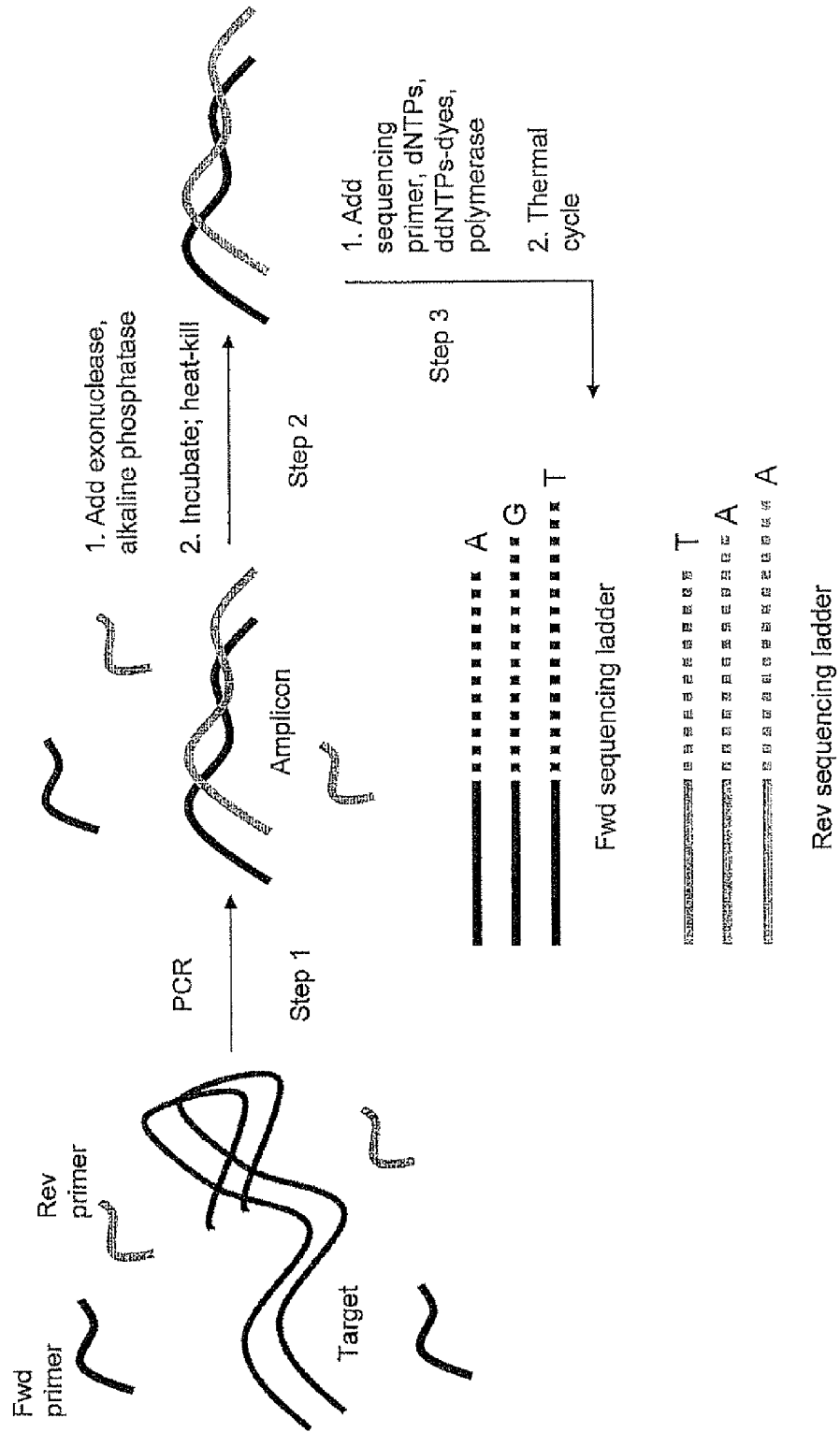
FIG. 1 is a diagrammatic representation of a standard PCR/cycle sequencing workflow requiring three steps.
Figure 2:
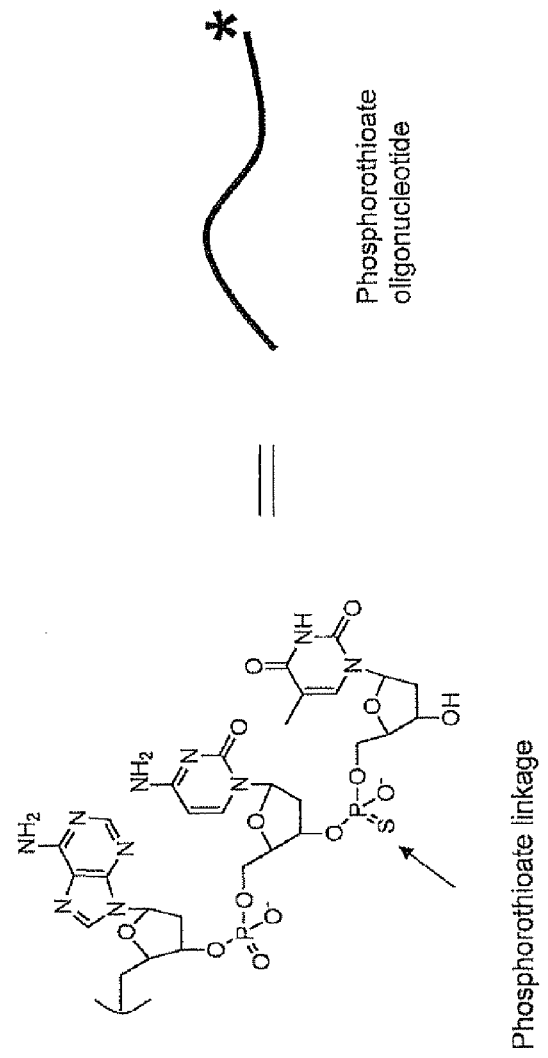
FIG. 2 illustrates an exonuclease I-resistant oligonucleotide having a phosphorothioate linkage at the terminal 3' end, according to various embodiments.
Figure 3:
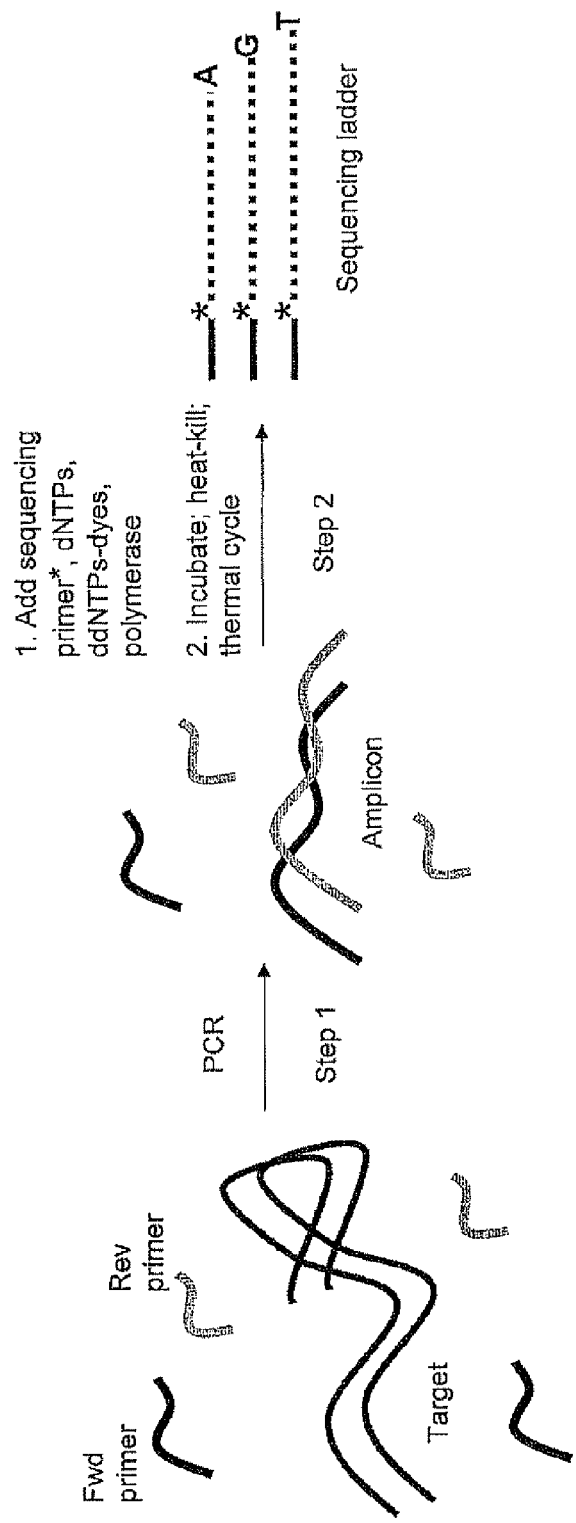
FIG. 3 illustrates a PCR/cycle sequencing workflow comprising two steps, utilizing a nuclease-resistant sequencing primer, according to various embodiments.

As used herein, the term "phosphorothioate linkage" refers to an inter-nucleotide linkage comprising a sulfur atom in place of a non-bridging oxygen atom within the phosphate linkages of a sugar phosphate backbone. The term phosphorothioate linkage refers to both phosphorothioate inter-nucleotide linkages and phosphorodithioate inter-nucleotide linkages. A "phosphorothioate linkage at a terminal 3' end" refers to a phosphorothioate linkage at the 3' terminus, that is, the last phosphate linkage of the sugar phosphate backbone at the 3' terminus. A phosphorothioate linkage at a terminal 3' end is illustrated in FIG. 2.

As used herein, the term "phosphodiester linkage" refers to the linkage —$PO_4$— which is used to link nucleotide monomers. Phosphodiester linkages as contemplated herein are linkages found in naturally-occurring DNA.

As used herein, the term "primer" refers to an oligonucleotide, typically between about 10 to 100 nucleotides in length, capable of selectively binding to a specified target nucleic acid or "template" by hybridizing with the template. The primer can provide a point of initiation for template-directed synthesis of a polynucleotide complementary to the template, which can take place in the presence of appropriate enzyme(s), cofactors, substrates such as nucleotides and oligonucleotides and the like.

As used herein, the term "sequencing primer" refers to an oligonucleotide primer that is used to initiate a sequencing reaction performed on a nucleic acid. The term "sequencing primer" refers to both a forward sequencing primer and to a reverse sequencing primer.

As used herein, the term "amplification primer" refers to an oligonucleotide, capable of annealing to an RNA or DNA region adjacent a target sequence, and serving as an initiation primer for DNA synthesis under suitable conditions well known in the art. Typically, a PCR reaction employs a pair of amplification primers including an "upstream" or "forward" primer and a "downstream" or "reverse" primer, which delimit a region of the RNA or DNA to be amplified.

As used herein, the term "tailed primer" or "tailed amplification primer" refers to a primer that includes at its 3' end a sequence capable of annealing to an RNA or DNA region adjacent a target sequence, and serving as an initiation primer for DNA synthesis under suitable conditions well known in the art. The primer includes its 5' end a sequence capable of annealing to a sequencing primer, for example, a universal sequencing primer.

As used herein, the term "amplifying" refers to a process whereby a portion of a nucleic acid is replicated. Unless specifically stated, "amplifying" refers to a single replication or to an arithmetic, logarithmic, or exponential amplification.

As used herein, the term "determining a nucleotide base sequence" or the term "determining information about a sequence" encompasses "sequence determination" and also encompasses other levels of information such as eliminating one or more possibilities for a sequence. It is noted that performing sequence determination of a polynucleotide typically yields equivalent information regarding the sequence of a perfectly complementary (100% complementary) polynucleotide and thus is equivalent to sequence determination performed directly on a perfectly complementary polynucleotide.

The term "nucleic acid sequence" as used herein can refer to the nucleic acid material itself and is not restricted to the sequence information (i.e. the succession of letters chosen among the five base letters A, C, G, T, or U) that biochemically characterizes a specific nucleic acid, for example, a DNA or RNA molecule. Nucleic acids shown herein are presented in a 5'→3' orientation unless otherwise indicated.

The term "fluorescent dye" as used herein refers to moieties that absorb light energy at a defined excitation wavelength and emit light energy at a different wavelength. Preferably the fluorescent dyes selected for use are spectrally resolvable. As used herein, "spectrally resolvable" means that the dyes can be distinguished on the basis of their spectral characteristics, particularly fluorescence emission wavelength, under conditions of operation. For example, the identity of the one or more terminal nucleotides can be correlated to a distinct wavelength of maximum light emission intensity, or perhaps a ratio of intensities at different wavelengths.

As used herein, the terms "polynucleotide", "nucleic acid", or "oligonucleotide" refers to a linear polymer of nucleosides (including deoxyribonucleosides, ribonucleosides, or analogs thereof) joined by inter-nucleosidic linkages. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage is typically a phosphodiester bond, and the subunits are referred to as "nucleotides." Oligonucleotide primers comprising other inter-nucleoside linkages, such as phosphorothioate linkages, are used in certain embodiments of the teachings. It will be appreciated that one or more of the subunits that make up such an oligonucleotide primer with a non-phosphodiester linkage can not comprise a phosphate group. Such analogs of nucleotides are considered to fall within the scope of the term "nucleotide" as used herein, and nucleic acids comprising one or more inter-nucleoside linkages that are not phosphodiester linkages are still referred to as "polynucleotides", "oligonucleotides", etc.

As used herein "sequence determination", "determining a nucleotide base sequence", "sequencing", and like terms includes determination of partial as well as full sequence information. That is, the term includes sequence comparisons, fingerprinting, and like levels of information about a target polynucleotide, as well as the express identification and ordering of each nucleoside of the target polynucleotide within a region of interest. In certain embodiments, "sequence determination" comprises identifying a single nucleotide, while in other embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary polynucleotide and thus is equivalent to sequence determination performed directly on a perfectly complementary polynucleotide.

As will be appreciated by one of ordinary skill in the art, references to templates, oligonucleotides, primers, etc., generally mean populations or pools of nucleic acid molecules that are substantially identical within a relevant region rather than single molecules. For example, a "template" generally means a plurality of substantially identical template molecules; a "primer" generally means a plurality of substantially identical primer molecules, and the like.

Cycle sequencing involves adding to a target nucleic acid or an amplification product thereof, sequencing primer, deoxynucleotide triphosphates (dNTPs), dye-labeled chain terminating nucleotides (e.g., dideoxynucleotide triphosphates (ddNTPs-dyes)), and DNA polymerase, followed by thermal cycle sequencing. Standard cycle sequencing procedures are well established. Cycle sequencing procedures are described in more detail, for example, in U.S. Pat. Nos. 5,741,676, and 5,756,285, each herein incorporated by reference in its entirety.

According to various embodiments of the present teachings, a method of preparing a nucleic acid for sequencing can comprise a step of amplifying the nucleic acid under conditions to produce amplification reaction products. The nucleic acid can be amplified using, for example, polymerase chain reaction. The nucleic acid can also be amplified using other methods such as, for example, multiple strand displacement amplification, helicase displacement amplification, nick translation, Q beta replicase amplification, rolling circle amplification, and other isothermal amplification methods.

According to various embodiments, the nucleic acid to be amplified can comprise, for example, DNA, cDNA, genomic DNA, viral DNA, plasmid DNA, recombinant DNA, amplicon DNA, or the like. Template molecules can be obtained from any of a variety of sources. For example, DNA can be isolated from a sample, which can be obtained or derived from a subject. The word "sample" is used in a broad sense to denote any source of a template on which sequence determination is to be performed. The phrase "derived from" is used to indicate that a sample and/or nucleic acids in a sample obtained directly from a subject can be further processed to obtain template molecules.

The source of a sample can be of any viral, prokaryotic, archaebacterial, or eukaryotic species. In certain embodiments the source can be a human. The sample can comprise, for example, blood or another body fluid containing cells, such as sperm, a biopsy sample, or the like. Mixtures of nucleic acids from different samples and/or subjects can be combined. Samples can be processed in any of a variety of ways. Nucleic acids can be isolated, purified, and/or amplified from a sample using known methods.

Amplifying nucleic acid can typically result in a reaction product that comprises excess amplification primer. According to various embodiments, a method of preparing nucleic acid for sequencing can comprise removing excess amplification primer from the reaction product. In some embodiments, the amplification primer can be removed, for example, by adding a nuclease enzyme and providing appropriate conditions for the nuclease to degrade the amplification primer. In some embodiments, the amplification primer can be removed by contacting the amplification reaction product with a reaction mixture comprising a nuclease enzyme. Nuclease suitable for use in the subject methods preferentially degrade single-stranded polynucleotides over double-stranded polynucleotides, thus destroying excess primers while leaving intact double-stranded amplicons for sequencing in subsequent steps. In various embodiments, the nuclease enzyme can comprise, for example, exonuclease I. Exonuclease I can be obtained from various commercial suppliers, for example from USB Corp., Cleveland, Ohio. Appropriate reaction conditions can include, for example, optimal time, temperature, and buffer parameters to provide for nuclease enzyme activity. In some embodiments, for example, excess amplification primer can be degraded by adding exonuclease I to the amplification reaction product and incubating at about 37° C. for about 30 min. Exonuclease I can hydrolyze single-stranded DNA in a 3'→5' direction.

According to various embodiments of a method for preparing a nucleic acid, a reaction mixture can further comprise a nuclease-resistant sequencing primer. The nuclease-resistant sequencing primer can be essentially non-degraded by a reaction mixture comprising nuclease, for example, exonuclease I, under reaction conditions at which excess amplification primer can be degraded by the nuclease. By "essentially non-degraded" it is intended that any degradation that takes place is not of a level that significantly interferes with the ability to generate sequencing data in the subsequent sequencing reactions.

According to various embodiments, the nuclease-resistant sequencing primer can comprise an oligonucleotide. In some embodiments, the nuclease-resistant sequencing primer can comprise one of more nuclease resistant internucleotide linkage. For example, the internucleotide linkage may be a phosphorothioate linkage. In some embodiments, the nuclease-resistant sequencing primer can comprise a I nuclease resistant internucleotide linkage at a terminal 3' end, at a terminal 5' end, and/or at one or more internal linkage sites. Nuclease-resistant sequencing primers may comprise one or more different types of nuclease resistant internucleotide linkages.

According to various embodiments, the nuclease-resistant sequencing primer can comprise a universal primer, for example, an M13 universal forward primer, an M13 universal reverse primer, or the like.

While embodiments of a method for preparing nucleic acid for sequencing can comprise using a phosphorothioated sequencing primer, and the teachings disclosed herein exemplify using a terminal 3' end phosphorothioated sequencing primer, other types of nuclease-resistant sequencing primers can be utilized within the scope of the present teachings. For example, a nuclease resistant sequencing primer can comprise an alkyl phosphonate monomer, RO—P(=O)(-Me)(—OR), such as dA-Me-phosphonamidite, and/or a triester monomer, RO—P(=O)(—OR')(—OR), such as dA-Me-phosphoramidite (available from Glen Research, Sterling, Va.), and/or a locked nucleic acid monomer (available from Exiqon, Woburn, Mass.), and/or a boranophosphate monomer, RO—P(—BH$_3$)(=O) (—OR), as described by Shaw, Barbara Ramsey, et al., in "Synthesis of Boron-Containing ADP and GDP Analogues: Nucleoside 5'-(P-Boraniodisphosphates)", Perspectives in Nucleoside and Nucleic Acid Chemistry, pg. 125-130, (2000), or the like.

According to various embodiments, the amplification reaction products can comprise a target amplicon. In some embodiments, the target amplicon can comprise a result of PCR amplification from amplification primers. In some embodiments, the target amplicon can comprise double stranded DNA. In some embodiments, the target amplicon can comprise single stranded DNA.

According to various embodiments, the amplification primers can comprise tailed primers. The tailed primers can be used, for example, to generate a target specific amplicon that incorporates nucleic acid sequence capable of annealing to a universal primer.

According to various embodiments, a method for preparing nucleic acid for sequencing can comprise inactivating a nuclease after excess primer is degraded by the nuclease. In some embodiments, the nuclease can be inactivated by heating. For example, the nuclease can be heat-inactivated by heating to a temperature of from about 80° C. to about 90° C. for about 15 minutes.

According to various embodiments of the present teachings, templates to be sequenced can be synthesized by PCR in individual aqueous compartments (also called "reactors") of an emulsion. In some embodiments, the compartments can each contain a particulate support such as a bead having a suitable first amplification primer attached thereto, a first copy of the template, a second amplification primer, and components needed for a PCR reaction (for example nucleotides, polymerase, cofactors, and the like). Methods for preparing emulsions are described, for example, in U.S. Pat. Nos. 6,489,103 B1, 5,830,663, and in U.S. Patent Application Publication No. US 2004/0253731. Methods for performing PCR within individual compartments of an emulsion to produce clonal populations of templates attached to microparticles are described, for example, in Dressman, D., et al, Proc. Natl. Acad. Sci., 100(15):8817-8822, 2003, and in PCT publication WO2005010145. All of the patents, applications, publications, and articles described herein are incorporated in their entireties by reference.

According to various embodiments, a method of sequencing nucleic acid can comprise amplifying nucleic acid in a first reaction mixture comprising nuclease sensitive amplification primers to form amplified nucleic acid, contacting the first reaction mixture with a second reaction mixture comprising a nuclease and a nuclease-resistant sequencing primer, under conditions in which the nuclease sensitive amplification primers are degraded by the nuclease, and inactivating the nuclease. The method can further comprise causing the amplified nucleic acid to react in a sequencing reaction under conditions in which the nuclease-resistant sequencing primer primes the sequencing reaction. According to various embodiments, results can be obtained based on the sequencing reaction and a nucleotide base sequence of the amplified nucleic acid can be determined based on the results.

According to various embodiments, the second reaction mixture can comprise nuclease-resistant sequencing primer, dNTPs, ddNTPs, and a thermo-stable DNA polymerase. In some embodiments, each of the ddNTPs can be labeled with a fluorescent dye (ddNTP-dye). For example, the ddNTPs can comprise BigDye ddNTPs, available from Applied Biosystems, Foster City, Calif. The thermo-stable DNA polymerase can comprise, for example, AmpliTaq polymerase, available from Applied Biosystems, Foster City, Calif. In some embodiments, the sequencing reaction can comprise a thermal cycle sequencing reaction.

According to various embodiments of a method for sequencing nucleic acid, the nuclease can comprise exonuclease I. The exonuclease I can be sensitive to heat inactivation and can be essentially 100 percent deactivated by heating, for example, heating at about 80° C. for about 15 minutes. Other heat inactivated nucleases may be used in the subject methods and compositions.

According to various embodiments, the nuclease-resistant sequencing primer can comprise at least one phosphorothioate linkage. In some embodiments, the nuclease-resistant sequencing primer can comprise at least one terminal 3' end phosphorothioate linkage.

According to various embodiments of the present teachings, a composition for sequencing nucleic acid can comprise a polymerase, a nuclease, a nuclease-resistant sequencing primer, dNTPs, and a chain terminator (e.g., ddNTPs). In some embodiments, the polymerase can comprise Taq polymerase, for example AmpliTaq polymerase. In some embodiments, the nuclease can comprise exonuclease I. In some embodiments, the nuclease-resistant sequencing primer can comprise at least one phosphorothioate linkage. In other embodiments, the nuclease-resistant sequencing primer can comprise a terminal 3' end phosphorothioate linkage. In some embodiments, the ddNTPs can comprise ddNTPs-dyes, for example fluorescent dye-labeled ddNTPs.

According to various embodiments, the composition can comprise a polymerase, for example a DNA polymerase, in an amount of from about 0.01 Unit to about 20 Units, for example, from about 0.1 Unit to about 1.0 Unit, or about 0.8 Unit. The composition can comprise polymerase in an amount within a range having an upper limit of from about 10 Units to about 20 Units and a lower limit of from about 0.01 Unit to about 0.05 Unit. According to various embodiments, the composition can comprise a nuclease, for example exonuclease I, in an amount of from about 1 Unit to about 40 Units, for example, from about 2 Units to about 15 Units, or about 10 Units. The composition can comprise nuclease in an amount within a range having an upper limit of from about 10 Units to about 40 Units, and a lower limit of from about 1 Unit to about 2 Units.

According to various embodiments, the composition can comprise a nuclease-resistant sequencing primer, in an amount of from about 0.1 µM to about 20 µM, for example about 1.0 µM. The composition can comprise a nuclease-resistant sequencing primer in an amount within a range having an upper limit of from about 10 µM to about 20 µM and a lower limit of from about 0.05 µM to about 0.1 µM. According to various embodiments, the composition can comprise dNTPs in an amount of from about 20 µM to about 5000 µM, for example, about 500 µM. The composition can comprise dNTPs in an amount within a range having an upper limit of from about 2000 µM to about 5000 µM and a lower limit of from about 20 µM to about 50 µM. According to various embodiments, the composition can comprise ddNTPs in an amount of from about 0.03 µM to about 10 µM, for example about 3 µM. The composition can comprise ddNTPs in an amount within a range having an upper limit of from about 5 µM to about 10 µM and a lower limit of from about 0.01 µM to about 0.05 µM. All molar amounts are based on final concentrations of the final volume.

According to various embodiments, the composition can comprise a non-nuclease-resistant amplification primer in an amount of from about 0.1 µM to about 20 µM, for example about 1.0 µM. The composition can comprise a non-nuclease-resistant amplification primer in an amount within a range having an upper limit of from about 10 µM to about 20 µM and a lower limit of from about 0.05 µM to about 0.1 µM. All molar amounts are based on final concentrations of the final volume.

According to various embodiments, the composition for sequencing nucleic acid can further comprise a PCR amplification product. In some embodiments, the PCR amplification product can comprise an amplified DNA target sequence. In some embodiments, the PCR amplification product can comprise non-nuclease-resistant amplification primer. The non-nuclease-resistant amplification primer can comprise, for example, phosphodiester linkages that are sensitive to degradation by exonuclease.

Examples of the methods of the present teachings are shown below. These examples are not limiting of the present teachings, and those of ordinary skill in the art will recognize that the components used in the reactions may be readily substituted with equivalent reagents known in the art.

The following Examples illustrate the stability of the phosphorothioate primer to exonuclease I, the incorporation of the phosphorothioate primer as a substrate for DNA polymerase, the compatibility of exonuclease I with the sequencing reagents, and the susceptibility of non-phosphorothioate primer to exonuclease I digestion. The Examples further illustrate the use of tailed amplification primers along with universal phosphorothioate primers for sequencing.

EXAMPLE 1

Two, 10 µL solutions containing pGEM-3Z (200 ng) (Promega Corp., Madison, Wis.), BigDye terminator (0.8 µL) (p/n 4337457, Applied Biosystems, Foster City, Calif.), 5× sequencing buffer (1.6 µL) (p/n 4305603, Applied Biosystems, Foster City, Calif.), M13 forward primer (1 µM) containing a terminal 3' phosphorothioate group indicated by an asterisk (TGTAAAACGACGGCCAG*T) (Seq ID No. 1), M13 reverse primer (1 µM) (CAGGAAACAGCTATGACC) (Seq ID No. 2), and either containing 10 Units of exonuclease I (p/n 70073Z, USB Corp., Cleveland, Ohio), or not containing exonuclease I, were prepared. The solutions were subjected to the following thermal cycling conditions on a Dual 384-Well GENEAMP® PCR System 9700 thermal cycler (p/n N8050002, Applied Biosystems, Foster City, Calif.): 37° C. for 30 minutes, 80° C. for 15 minutes; then 25 cycles of 96° C. for 10 seconds, 50° C. for 5 seconds, and 60° C. for 2 minutes. The samples were ethanol precipitated and loaded on a DNA sequencer (Model 3730, Applied Biosystems, Foster City, Calif.).

Figure 4:
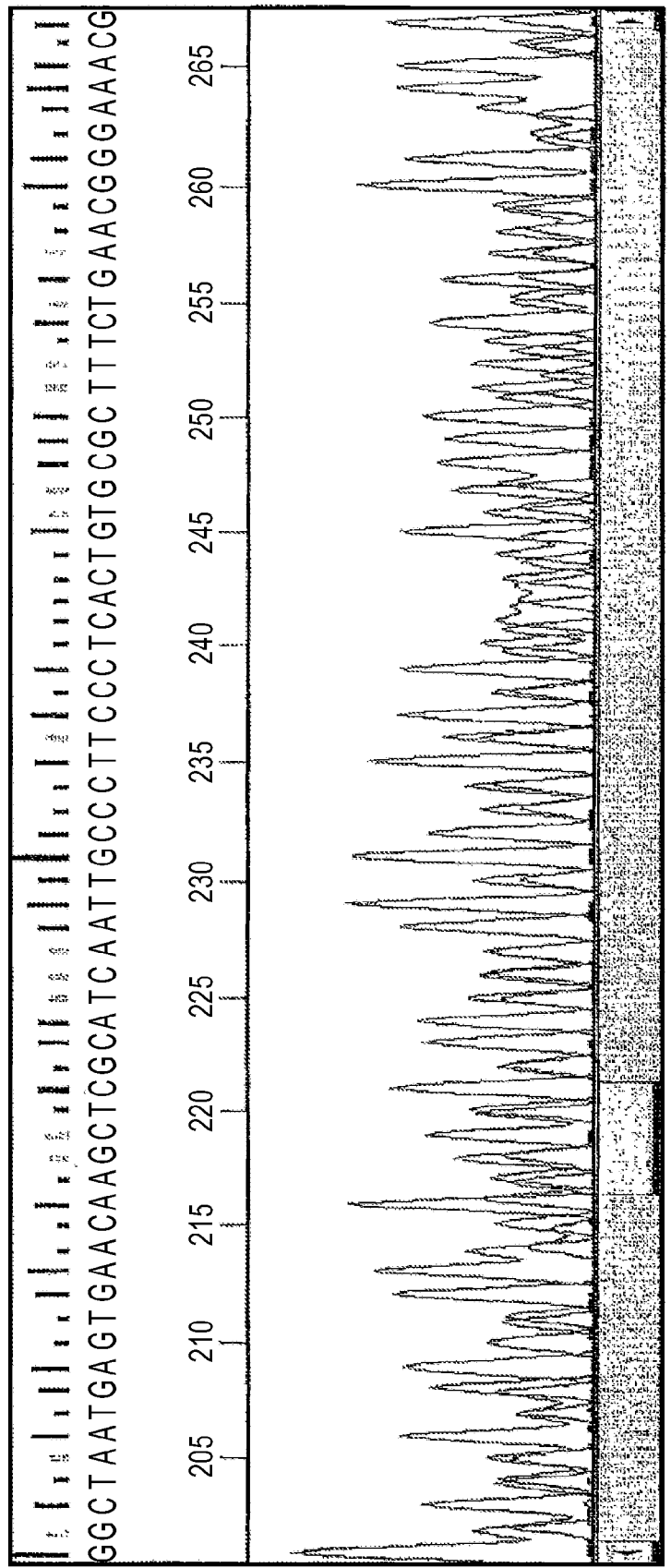
FIG. 4 is a DNA sequence electropherogram of pGEM-3Z plasmid DNA showing overlapping sequence data generated from both M13 forward and M13 reverse sequencing primers.
Figure 5:
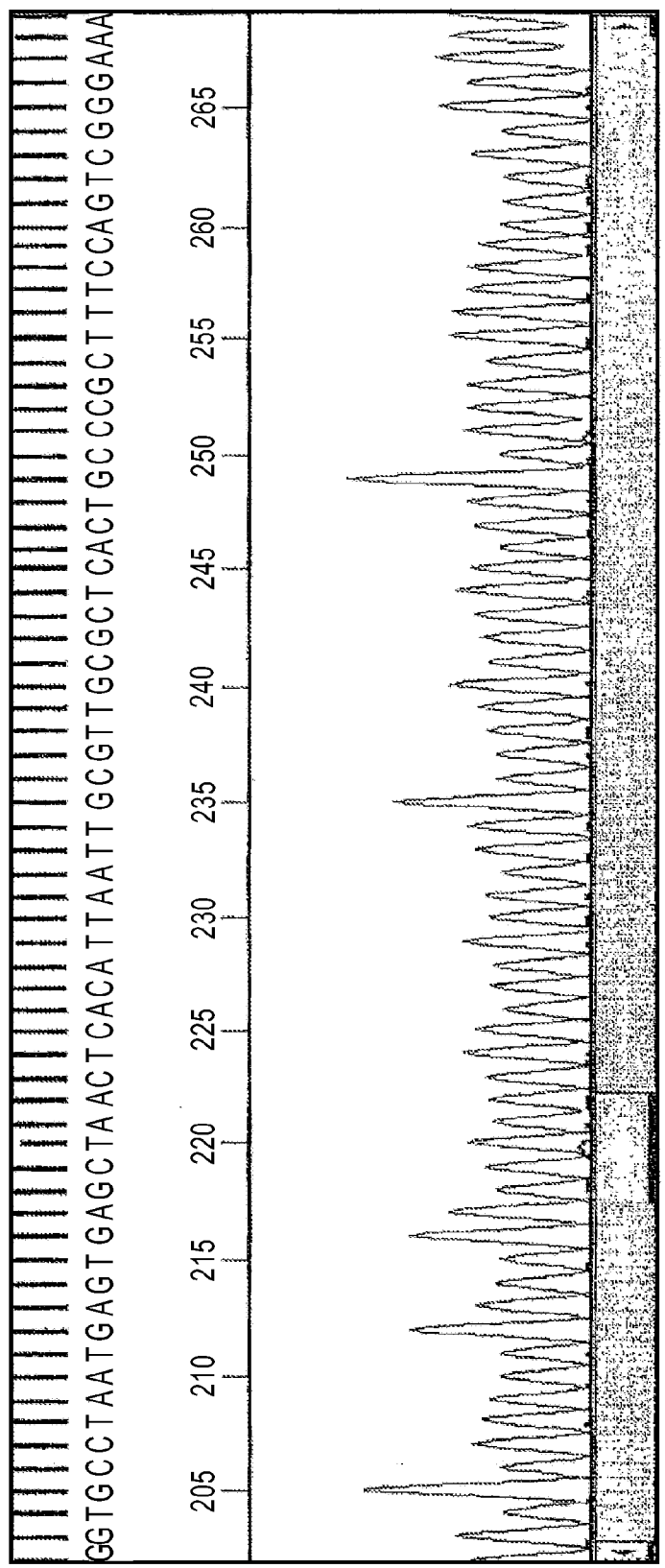
FIG. 5 is a DNA sequence electropherogram of the pGEM-3Z plasmid DNA used to generate the electropherogram of FIG. 4, but showing clean sequence data generated from sequencing with a phosphorothioated M13 forward sequencing primer and using exonuclease.

FIG. 4 and FIG. 5 show sequence data for the two samples. FIG. 4 shows an electropherogram for the sample without exonuclease I. Overlapping sequence data generated from both M13 forward and M13 reverse primers is clearly illustrated. FIG. 5 shows an electropherogram for the sample with exonuclease. Clear and clean sequence data generated from the phosphorothioated M13 forward primer is demonstrated in FIG. 5.

EXAMPLE 2

Figure 6:
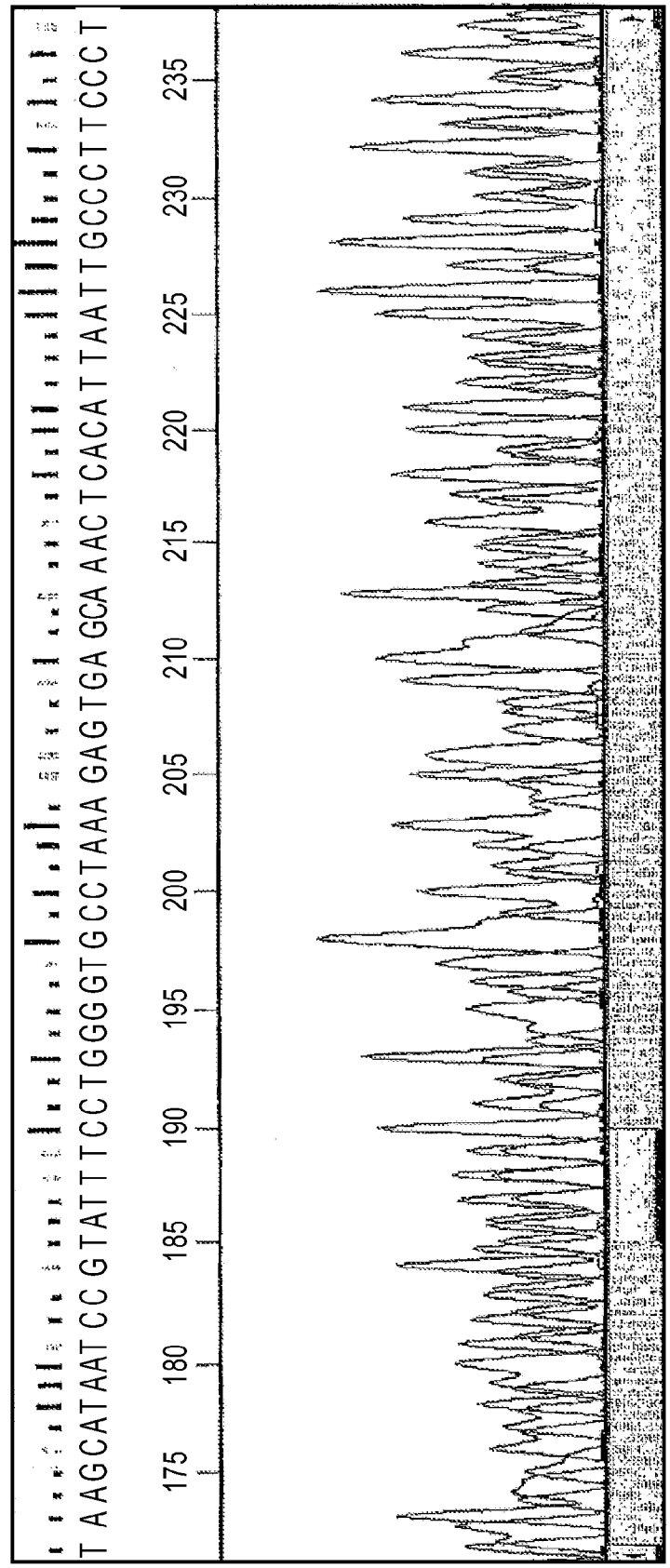
FIG. 6 is a DNA sequence electropherogram of pGEM3-Z3 plasmid DNA showing overlapping sequence data generated from both M13 forward and M13 reverse sequencing primers.
Figure 7:
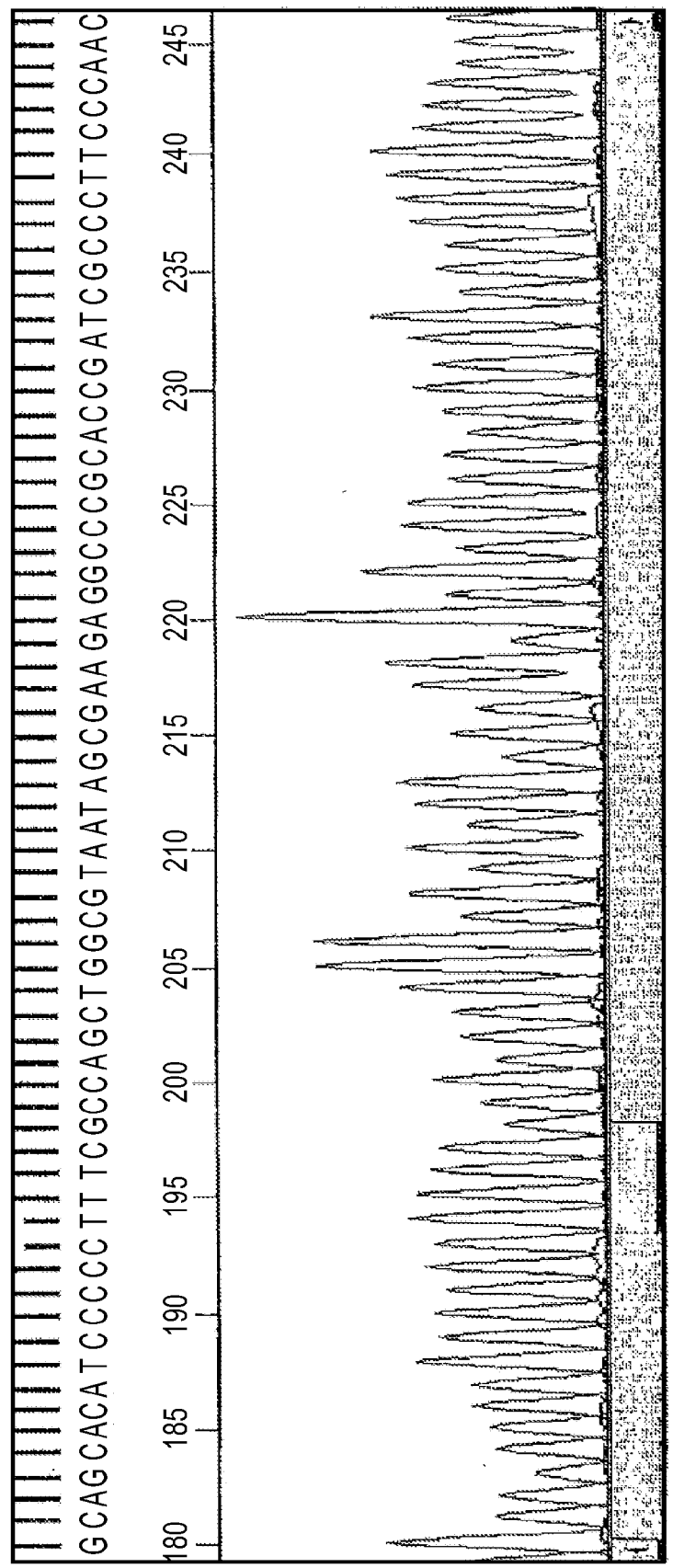
FIG. 7 is a DNA sequence electropherogram of the pGEM3-Z3 plasmid DNA used to generate the electropherogram of FIG. 6, but showing clean sequence data generated from sequencing with a phosphorothioated M13 reverse sequencing primer and using exonuclease.
Figure 8:
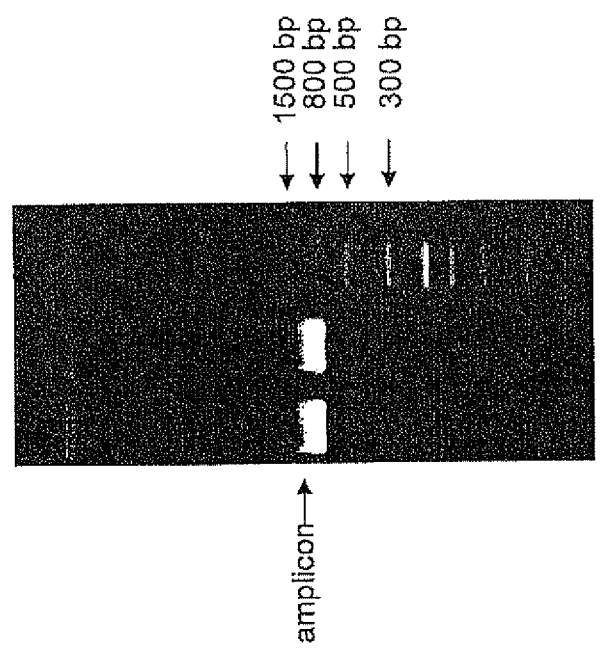
FIG. 8 is a representation of an amplicon and a size standard.

This example was performed essentially identically to Example 1, but with a phosphorothioated M13 reverse primer (CAGGAAACAGCTATGAC*C) (Seq ID No. 3), and a non-phosphorothioated M13 forward primer (TGTAAAAC-GACGGCCAGT) (Seq ID No. 4). FIGS. 6 and 7 show sequence data for the two samples without and with exonuclease I, respectively. As can be seen, for the sample without exonuclease I, overlapping sequence data generated from both M13 forward and reverse primers is shown in FIG. 6, while clear and clean sequence data generated from only the phosphorothioated M13 reverse primer is shown in FIG. 7.

EXAMPLE 3

This example further demonstrates the application of phosphorothioated sequencing primers and exonuclease I treatment to the sequencing of PCR-generated amplicons. This example also demonstrates a shortened PCR/cycle sequencing workflow using a mixture of exonuclease I, phosphorothioate primer, and BigDye terminator.

Amplification

PCR reactions were carried out in the following 10 µL solution: Power SYBR Green PCR Master Mix (5 µL) (p/n 4368706, Applied Biosystems, Foster City, Calif.), primers LGL002 (GGTAGTGCCCAAACGCTCA) (Seq. ID No. 5) and LGL005 (GCCTTATCGCTGGGAAATCA) (Seq. ID No. 6) (200 nM each) target H17-1 (approximately 12 copies per well), and water. PCR was carried out in separate wells of a 384-well plate using an ABI 7900 sequence detection system. The following thermal cycling on a Dual 384-Well GENEAMP® PCR System 9700 thermal cycler (p/n N8050002, Applied Biosystems, Foster City, Calif.) was used: 95° C. for 10 minutes, then 50 cycles of 95° C. for 15 seconds, 50° C. for 15 seconds, and 65° C. for 2 minutes. A few representative wells (5 µL) were analyzed on an agarose gel. A band consistent with the expected 749 bp amplicon was observed.

H17-1 is pGEM-3Z plasmid containing a 762 bp cloned insert (Seq. ID No. 7). Amplification primer binding sites for LGL005, and LGL002 (reverse complement), are underlined.

```
                                              (Seq ID No. 7)
CCCGTCGCCTTATCGCTGGGAAATCAGGTATCGAATCTTTTAGC

TCGTACCATGTCCTGATACAGGGCTTGATAATCATTTTCTGAAT

ACATTTTCGCGATACCGTCCAGCGACATTCTTCCTCGGTACATA

ATCTCCTTTGGCGTTTCCCGATGTCCGTCACGCACATGGATCC

CGTGATGACCTCATTAAAAACACGCTGCAATCCCTCCTCATCTT

TGCAGGCAAGTCCGATTTTTTGCGTTGATTTTTTAATGCAGAAT

ATGCAGTTACCGAGATGTTCCGGTATTTGCAAATCGAATGGTTG

TTGCTTCCACCATGCGAGGATATCTTCCTTCTCAAAGTCTGACA

GTTCAGCAAGATATCTGATTCCAGGCTTTGGCTTTAGCCGCTTC

GGTTCATCAGCTCTGATGCCAATCCACGTGGTGTAATTCCCTCG

CCCGAAATGGTCATCACAGTATTTGGTGAAGGGAACGAGTTTTA

ATCTGTCAGTGCAGAACGCGCCGCCGACGTATGGAGTGCCATAT

TTCTTTACCATATCGATAAATGGCTTCAGAACAGGCATTCGCGT

CTGAATATCCTTCGGTTCCCATACCGTATAACCATTTGGCTGTC

CAAGCTCCGGGTTGATATCAACCTGCAATACGGTGAGCGGTATA

TCCCAGAACTTCACAACTTCCCTGACAAACCGATATGTCATTGG

ATGTTCACAACCTGTATCCATGAAAACGTAATTGAGCGTTTGGG

CACTACCATGCGAT.
```

Sequencing

Two, 6 µL solutions, each containing H-17 PCR amplicon (1.0 µL), BigDye Terminator v3.1 (0.8 µL) (Applied Biosystems, Foster City, Calif.), 5x sequencing buffer (0.8 µL), LGL017 primer (1 µM) containing a terminal 3' phosphorothioate group indicated by an asterisk (GGTAGTGCCCAAACGCTC*A) (Seq. ID No. 8), water and either exonuclease I (2 units) tin 70073Z, USB Corp., Cleveland, Ohio) or not containing exonuclease I, were prepared. The reactions were placed in separate wells of a 384-well plate and thermally cycled on a Dual 384-Well Gene-Amp PCR System 9700 thermal cycler (Applied Biosystems, Foster City, Calif.) using the following thermal cycling conditions: 37° C. for 15 minutes, 80° C. for 15 minutes, 96° C. for 1 minute; then 25 cycles of 96° C. for 10 seconds, 50° C. for 5 seconds, 60° C. for 2 minutes; and then 4° C. indefinite hold.

Excess salt and dye terminators were removed by ethanol precipitation as follows: 25 µL of a solution of 85% ethanol/ 0.12 M sodium acetate were added to each well and the plate was centrifuged at 2500 times (x) the force of gravity (g) for 30 minutes. The solution was removed by inverting the plate onto a paper towel and centrifuging at 180xg for 1 minute. To each well was added 30 µL of 70% ethanol and the plate was centrifuged at 1650xg for 15 minutes. The solution was removed by inverting the plate onto a paper towel and centrifuging at 180xg for 1 minute. The precipitated sequencing reaction was then dissolved in 10 µL of 50 µMEDIA and loaded onto an AB 3730 DNA analyzer equipped with a 50 cm capillary array (Applied Biosystems, Foster City, Calif.).

Figure 9:
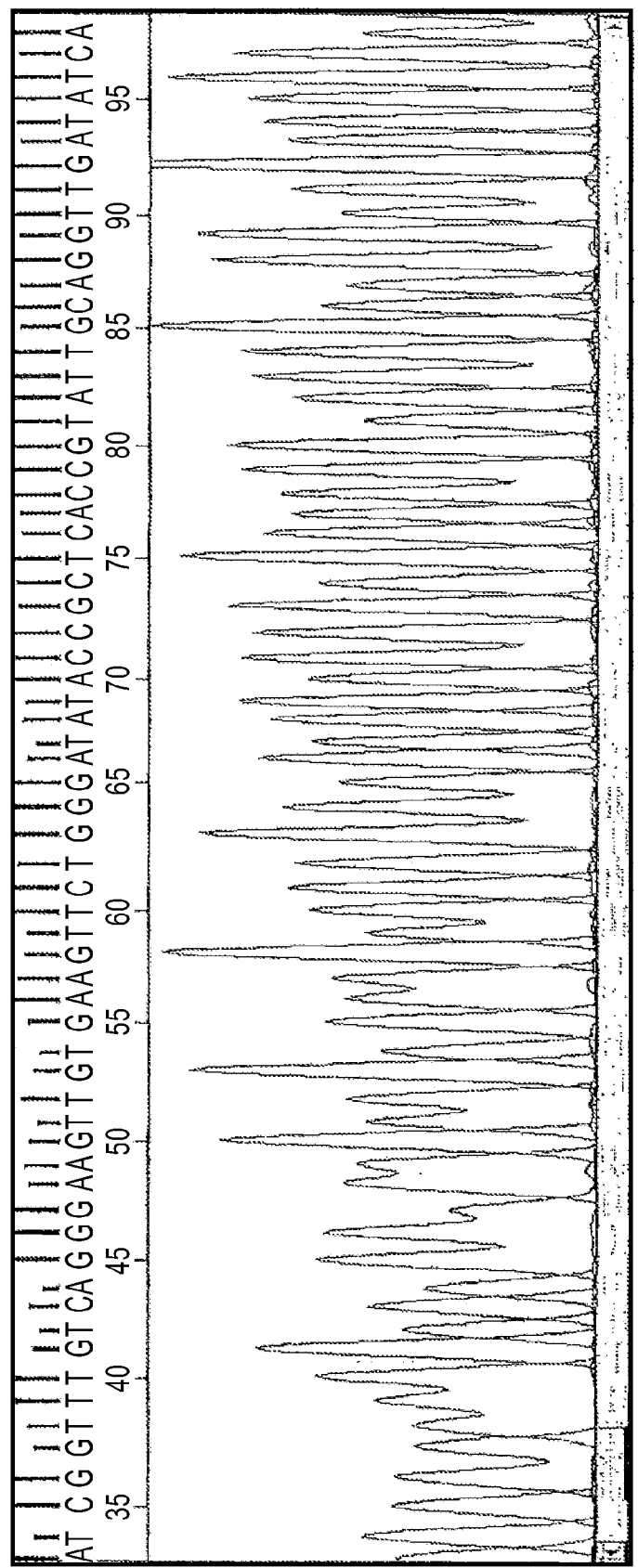
FIG. 9 is a DNA sequence electropherogram of a PCR amplicon treated with exonuclease I, showing clean sequence data generated from sequencing with a phosphorothioated sequencing primer.
Figure 10:
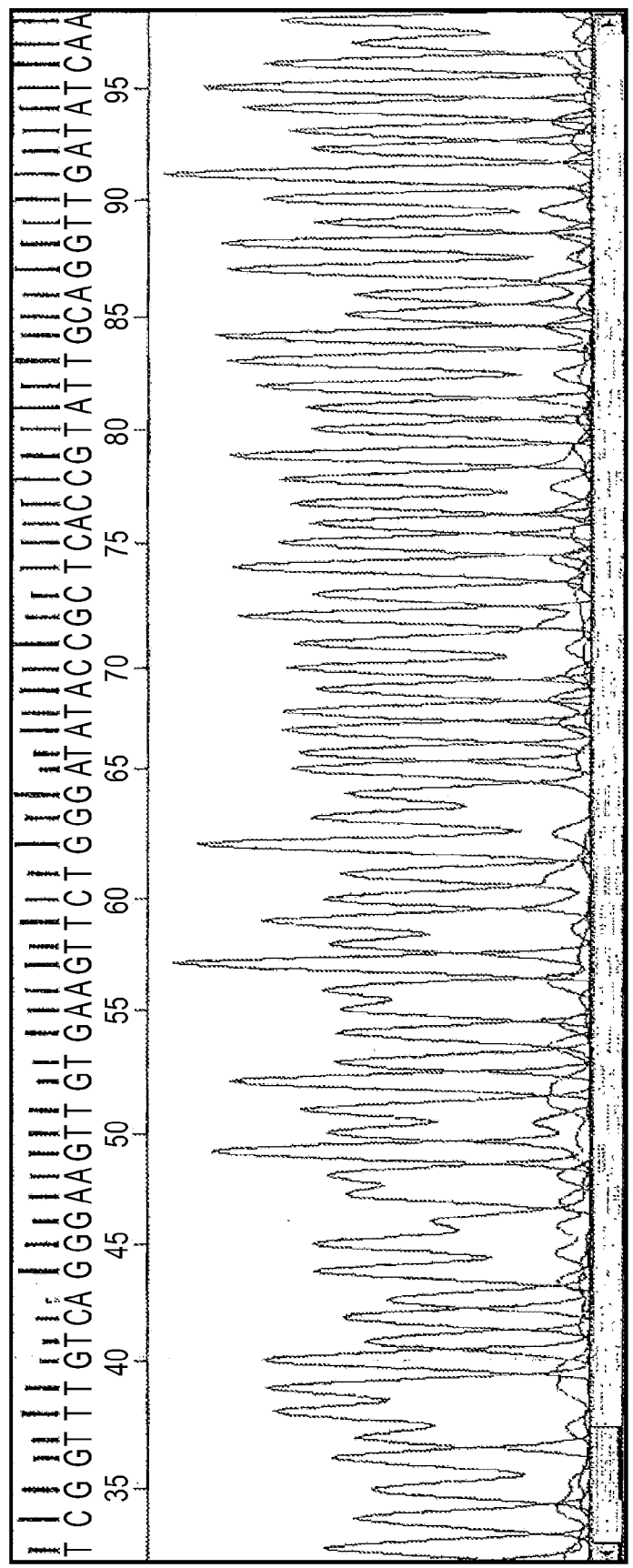
FIG. 10 is a DNA sequence electropherogram of the PCR amplicon used to generate the electropherogram of FIG. 9, but sequenced without using exonuclease I.

FIG. 9 and FIG. 10 show sequencing results from two representative samples. FIG. 9 and FIG. 10 show respective electropherograms produced from a sample treated with and without exonuclease I, respectively. As shown in FIG. 9, clear, clean, and correct sequence data are generated from PCR amplified amplicon treated with exonuclease I, from phosphorothioated LGL017 primer. In contrast, as shown in FIG. 10, a level of underlying noise is prominently seen in the sequence data generated from the same amplicon but untreated with exonuclease I.

EXAMPLE 4

This example demonstrates the application of tailed PCR amplification primers in combination with phosphorothioated universal sequencing primers and exonuclease I treatment. This example further demonstrates a simplified PCR/cycle sequencing workflow using only one set of forward and/or reverse phosphorothioate sequencing primers.

Amplification

Three PCR reactions were performed in three wells of a 96-well plate. Each reaction contained the following: Amplitaq Gold® PCR Master Mix (1 µL) (p/n 4327058, Applied Biosystems, Foster City, Calif.), PCR "C" forward primer (TGTAAAACGACGGCCAGTGGCTCCTG-GCACAAAGCTGG) (Seq. ID No. 9) and PCR "C" reverse primer (CAGGAAACAGCTATGACCTGCATCTCAT-TCTCCAGGCTTCA) (Seq. ID No. 10) (120 nM each), genomic DNA (2 ng), glycerol (8% v/v) and water (total aqueous volume 2 µL). The aqueous layer was overlaid with 10 µL of silicone oil (viscosity 5 cSt, p/n 317667, Sigma-Aldrich Co., St. Louis, Mo.). PCR was carried out using an ABI 9700 thermal cycler (Applied Biosystems, Foster City, Calif.) with the following thermal cycle conditions: 96° C. for 5 minutes; then 40 cycles of 94° C. for 30 seconds, 60° C. for 45 seconds, and 72° C. for 45 seconds; then a final 72° C. for 10 minutes and 4° C. for indefinite hold.

To one well was added 2x loading buffer (5 µL), and the total aqueous solution was analyzed on an agarose gel. A band consistent with a 630 bp amplicon was observed (result not shown).

Amplicon C (Seq. ID No. 11) is shown below with primer binding sites for PCR "C" forward primer, and PCR "C" reverse primer (reverse complement) underlined.

```
                                              (Seq. ID No. 11)
TGTAAAACGACGGCCAGTGGCTCCTGGCACAAAGCTGGAC

AGTCGCCATGACAAGTAAGGGCAAGTAATCCGCCTGCCGG

AGGAAGCAAAGGAAATGGAGTTGGGGAGGAGGGTGCAGAG

TCAGGATTCTCGCCGACCTGGTGCCGTAGATACTAACATT

TTGGGGTGGAAAATTCTGCAAGCCAGAGCTGTGAGGGCAG

AATTGGTGGAAATCATTTTGGAGGAATCCTGCATTGTGTC

AAATATGAAGGGTGGAAGGAAGAAAGCTTTTGCGTTTGCT

CTCAGCTGGATCCTTTCTTCTCATCAGTTAAAATGTCATT
```

-continued

```
TTTTAGGAAGGCTTTCCGTAATATCACACCCTAACGTTTT

CTCCCAGATACTTTATATCACACCATCTTATTTAATCTCC

TTCACAACCCTTATCACTCTGATAAGATTTATTTGTTCAT

TGCTTTCAGTACATGGAAACGTAAGCCTTATGAGGATATA

GAATTTTTCTACTATCTTATTCATTGTTGTATTCCTGAGT

GCCTATATCAGTGCTGGGTAGCAAGTAAGAGCTCGATAAT

AAATATTTTTTGAATGAGGGAGACAGGTCTGAAGCCTGGA

GAATGAGATGCAGGTCATAGCTGTTTCCTG.
```

Sequencing

To the two remaining wells containing Amplicon C were added 6 μL of a solution containing BigDye® Terminator v3.1 (0.8 μL) (p/n 4337457, Applied Biosystems, Foster City, Calif.), LGL019 universal primer (1 μM) containing a terminal 3' phosphorothioate group indicated by an asterisk (TGTAAAACGACGGCCAG*T) (Seq. ID No. 12), 5× sequencing buffer (0.8 μL) (p/n 4305603, Applied Biosystems, Foster City, Calif.), water, and either exonuclease I (2 units) (p/n 70073Z, USP Corp., Cleveland, Ohio), or not. The samples were thermally cycled on a GeneAmp® PCR System 9700 thermal cycler (p/n N8050200, Applied Biosystems, Foster City, Calif.) using the following thermal cycle conditions: 37° C. for 15 minutes, 80° C. for 15 minutes; then 96° C. for 1 minute; then 25 cycles of 96° C. for 10 seconds, 50° C. for 5 seconds, 60° C. for 2 minutes; and then 4° C. indefinite hold.

Excess salt and dye terminators were removed using a BigDye® XTerminator™ Purification Kit t/n 4376484, Applied Biosystems, Foster City, Calif.). SAM™ solution (36 μL) (Applied Biosystems, Foster City, Calif.) and Xterminator™ (8 μL) (Applied Biosystems, Foster City, Calif.) were added to each well, the plate was heat-sealed, and vortexed for 30 minutes. The samples were loaded onto an AB 3730 DNA Analyzer (Applied Biosystems, Foster City, Calif.) equipped with a 50 cm capillary array and BigDye Xterminator run module (Applied Biosystems, Foster City, Calif.).

Figure 11:
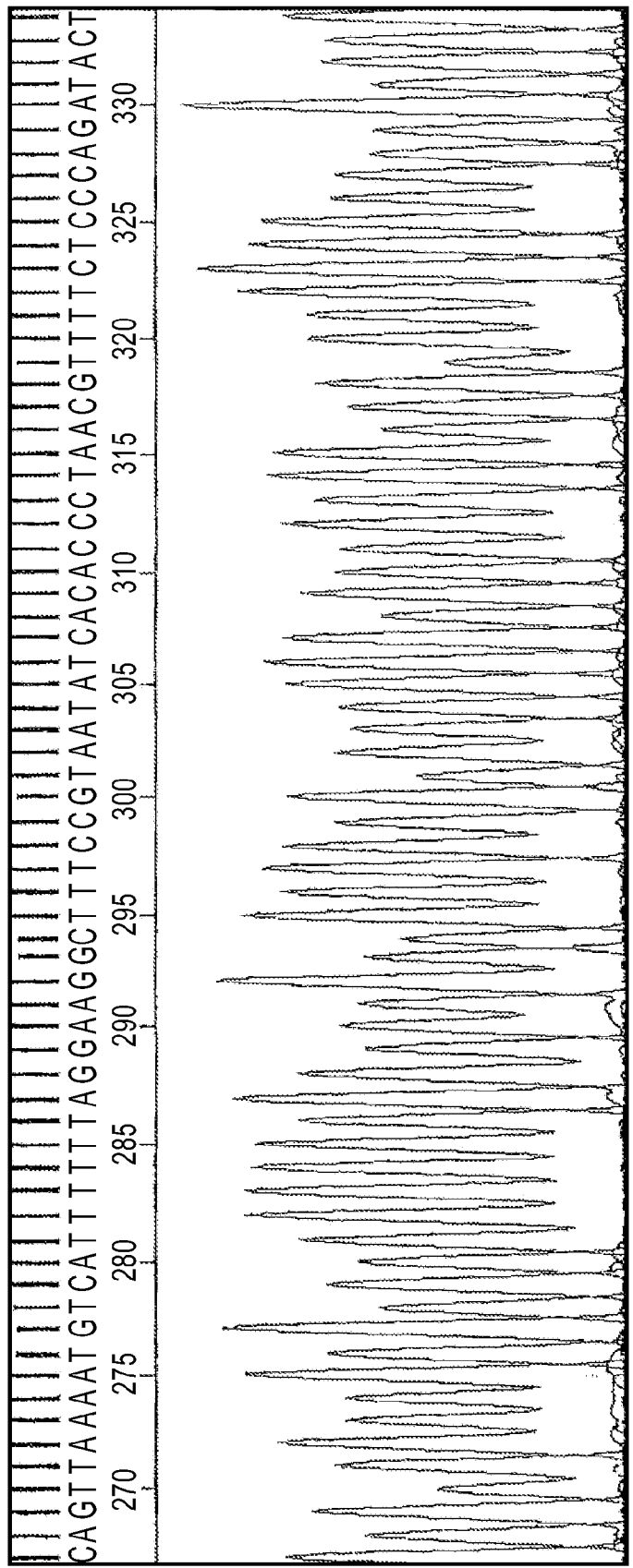
FIG. 11 is a DNA sequence electropherogram of a PCR amplicon generated from tailed amplification primers, treated with exonuclease I, showing clean sequence data generated from sequencing with a phosphorothioated universal sequencing primer.
Figure 12:
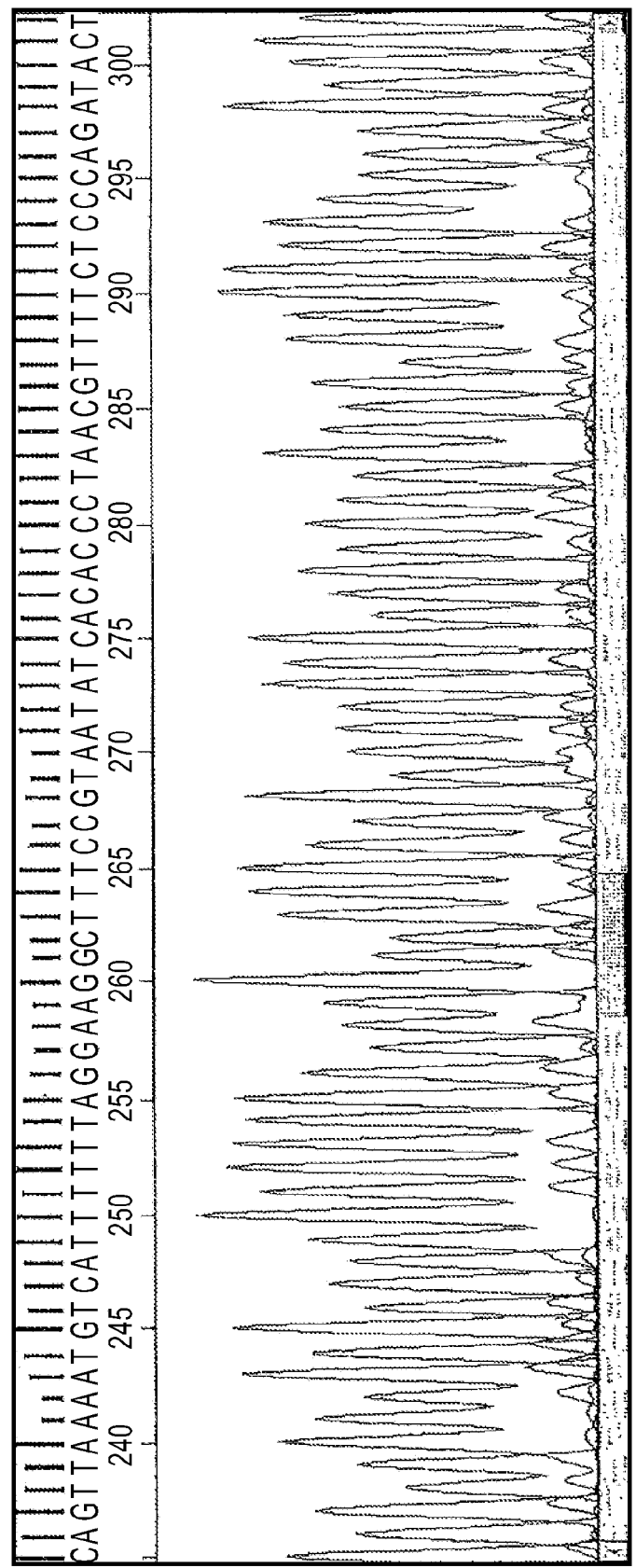
FIG. 12 is a DNA sequence electropherogram of the PCR amplicon used to generate the electropherogram of FIG. 11, but sequenced without using exonuclease I.

FIG. 11 and FIG. 12 show sequencing results from the two samples. FIGS. 11 and 12 show respective electropherograms produced from the samples treated with exonuclease I (FIG. 11) and untreated (FIG. 12). As shown in FIG. 11, clear, clean, and correct sequence data are generated from tailed PCR amplification primer amplified amplicon treated with exonuclease I, in combination with phosphorothioated LGL019 primer (M13 forward universal primer). In contrast, as shown in FIG. 12, a level of underlying noise is prominently seen in the sequence data generated from the same amplicon but untreated with exonuclease I.

Although only a few embodiments have been described in detail above, those having ordinary skill in the molecular biology and chemistry arts will clearly understand that modifications are possible in the various embodiments without departing from the present teachings.

What is claimed is:

1. A method of preparing DNA for sequencing, comprising the steps of:
    amplifying the DNA under conditions to produce amplification reaction products, the amplification reaction products comprising excess amplification primer; and
    contacting said amplification reaction products with a nucleic acid sequencing reaction mixture comprising a polymerase, a nuclease, a nuclease-resistant sequencing primer, deoxynucleotide triphosphates, and dideoxynucleotide triphosphates under conditions in which the excess amplification primer is degraded by the nuclease and the nuclease-resistant sequencing primer is essentially non-degraded.

2. The method of claim 1, wherein the amplification reaction products further comprise a target amplicon.

3. The method of claim 1, further comprising inactivating the nuclease after the excess amplification primer is degraded by the nuclease.

4. The method of claim 3, wherein inactivating the nuclease comprises heating.

5. The method of claim 1, wherein the nuclease comprises exonuclease I.

6. The method of claim 1, wherein the nuclease-resistant sequencing primer comprises at least one phosphorothioate linkage.

7. The method of claim 1, wherein the nuclease-resistant sequencing primer comprises a phosphorothioate linkage at a terminal 3' end of the sequencing primer.

8. A method for sequencing DNA, comprising the steps of:
amplifying DNA in a first reaction mixture comprising nuclease-sensitive amplification primers to form amplified DNA;
contacting said first reaction mixture of the amplifying step with a second reaction mixture comprising a polymerase, a nuclease, a nuclease-resistant sequencing primer, deoxynucleotide triphosphates, and dideoxynucleotide triphosphates, under conditions in which the nuclease sensitive amplification primers are degraded by the nuclease;
inactivating the nuclease; and
causing the amplified DNA to react in a sequencing reaction under conditions in which the nuclease-resistant sequencing primer primes said sequencing reaction.

9. The method of claim 8, further comprising:
obtaining results based on the sequencing reaction; and
determining a nucleotide base sequence of the amplified DNA based on the results.

10. The method of claim 8, wherein amplifying DNA comprises polymerase chain reaction amplification.

11. The method of claim 8, wherein the nuclease comprises exonuclease I.

12. The method of claim 8, wherein the nuclease-resistant sequencing primer comprises at least one phosphorothioate linkage.

13. The method of claim 12, wherein the nuclease-resistant sequencing primer comprises a phosphorothioate linkage at a terminal 3' end.

14. The method of claim 8, wherein inactivating the nuclease comprises heating.

15. The method of claim 8, wherein the sequencing reaction comprises cycle sequencing.

16. The method of claim 8, wherein the dideoxynucleotide triphosphates comprise dye-labeled dideoxynucleotide triphosphates.

17. A composition for sequencing nucleic acid, comprising: a polymerase, a nuclease, a nuclease-resistant sequencing primer, deoxynucleotide triphosphates, and dideoxynucleotide triphosphates.

18. The composition of claim 17, further comprising PCR amplification reaction product that comprises non-nuclease-resistant amplification primer.

19. The composition of claim 18, wherein the PCR amplification reaction product further comprises an amplified DNA target sequence.

20. The composition of claim 17, wherein the polymerase is Taq polymerase.

21. The composition of claim 17, wherein the nuclease comprises exonuclease I.

22. The composition of claim 17, wherein the nuclease-resistant primer comprises at least one phosphorothioate linkage.

23. The composition of claim 22, wherein the nuclease-resistant primer comprises a phosphorothioate linkage at a terminal 3' end of the primer.

24. The composition of claim 17, wherein the nuclease-resistant primer comprises an exonuclease I resistant primer.

25. The composition of claim 17, wherein the dideoxynucleotide triphosphates comprise dye-labeled dideoxynucleotide triphosphates.

26. The composition of claim 25, wherein the dye-labeled dideoxynucleotide triphosphates comprise fluorescent dye-labeled dideoxynucleotide triphosphates.

* * * * *